United States Patent
Kim et al.

(10) Patent No.: US 11,291,694 B2
(45) Date of Patent: *Apr. 5, 2022

(54) **COMPOSITION FOR TREATING OR PREVENTING METABOLIC DISEASE, CONTAINING, AS ACTIVE INGREDIENT, EXTRACELLULAR VESICLES DERIVED FROM *AKKERMANSIA MUCINIPHILA* BACTERIA**

(71) Applicant: MD HEALTHCARE INC., Seoul (KR)

(72) Inventors: Yoon-Keun Kim, Paju-si (KR); Hyun-Taek Park, Ulsan (KR)

(73) Assignee: MD HEALTHCARE INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/824,111

(22) Filed: Mar. 19, 2020

(65) Prior Publication Data

US 2020/0222470 A1 Jul. 16, 2020

Related U.S. Application Data

(63) Continuation of application No. 15/312,419, filed as application No. PCT/KR2015/004983 on May 19, 2015, now abandoned.

(30) Foreign Application Priority Data

May 20, 2014 (KR) .......................... 10-2014-0060409
May 18, 2015 (KR) .......................... 10-2015-0068864

(51) Int. Cl.
| | |
|---|---|
| *A61P 1/00* | (2006.01) |
| *A61K 8/99* | (2017.01) |
| *A61K 35/74* | (2015.01) |
| *A23L 33/10* | (2016.01) |
| *A23L 33/135* | (2016.01) |

(52) U.S. Cl.
CPC .............. *A61K 35/74* (2013.01); *A23L 33/10* (2016.08); *A23L 33/135* (2016.08); *A23V 2002/00* (2013.01)

(58) Field of Classification Search
None
See application file for complete search history.

(56) References Cited

U.S. PATENT DOCUMENTS

| | | | |
|---|---|---|---|
| 2012/0058094 A1* | 3/2012 | Blaser .................. | A61K 9/0053 424/93.41 |
| 2012/0222142 A1 | 8/2012 | Kim et al. | |
| 2013/0224155 A1 | 8/2013 | Kaplan et al. | |
| 2017/0087195 A1* | 3/2017 | Kim ....................... | A61K 35/74 |

FOREIGN PATENT DOCUMENTS

| | | |
|---|---|---|
| KR | 10-2010-0120846 A | 11/2010 |
| KR | 10-2013-0021920 A | 3/2013 |
| WO | 2014/019271 A1 | 2/2014 |

OTHER PUBLICATIONS

Kang et al., "Extracellular Vesicles Derived from Gut Microbiota, Especially Akkermansia muciniphila, Protect the Progression of Dextran Sulfate Sodium-Induced Colitis", PLOS One, 2013, vol. 8, No. 10, pp. 1-11 (Year: 2013).*
Everard et al., "Cross-talk between Akkermansia muciniphila and intestinal epithelium controls diet-induced obesity", PNAS, vol. 110, No. 22, May 28, 2013 (Year: 2013).*
Hansen et al., "Early life treatment with vancomycin propagates Akkermansia muciniphila and reduces diabetes incidence in the NOD mouse", Diabetologia, 2012, vol. 55, pp. 2285-2294.
International Search Report dated Aug. 27, 2015 of PCT/KR2015/004983 which is the parent application and its English translation—6 pages.
English translation of KR20130021920 A obtained from KIPO on Dec. 4, 2017. (Year: 2017).

* cited by examiner

*Primary Examiner* — Robert T. Crow
*Assistant Examiner* — John P Nguyen
(74) *Attorney, Agent, or Firm* — Vorys, Sater, Seymour & Pease LLP; Mih Suhn Koh

(57) ABSTRACT

The present invention relates to a pharmaceutical and food composition for treating, preventing, or alleviating a metabolic disease, containing, as an active ingredient, extracellular vesicles derived from *Akkermansia muciniphila*. The composition of the present invention can be used as a pharmaceutical/food composition and the like for treating, preventing, or alleviating metabolic diseases, in particular metabolic diseases such as obesity, diabetes, hyperlipidemia, arteriosclerosis, and hypertension, occurring or exacerbated due to a high fat diet. In addition, in the present invention, a fermented food itself, prepared by adding *Akkermansia muciniphila*, can be used for the purpose of preventing or alleviating a metabolic disease occurring or exacerbated due to a high fat diet.

1 Claim, 18 Drawing Sheets

COMPOSITION FOR TREATING OR PREVENTING METABOLIC DISEASE, CONTAINING, AS ACTIVE INGREDIENT, EXTRACELLULAR VESICLES DERIVED FROM *AKKERMANSIA MUCINIPHILA* BACTERIA

CROSS-REFERENCE TO RELATED APPLICATIONS

This application is a Continuation Application of U.S. patent application Ser. No. 15/312,419, filed Nov. 18, 2016, which was a 371 of PCT/KR2015/004983, filed May 19, 2015, which claims the benefit of priority from Korean Patent Application No. 10-2014-0060409, filed May 20, 2014, and from Korean Patent Application No. 10-2015-0068864, filed May 18, 2015, the contents of each of which are incorporated herein by reference in its entirety.

TECHNICAL FIELD

The present invention relates to a pharmaceutical and food composition containing extracellular vesicles derived from *Akkermansia muciniphila* as an active ingredient for treating, preventing or alleviating a metabolic disease.

BACKGROUND ART

A metabolic disease is a general term for diseases that occur due to in vivo metabolic disorders. The metabolic disease generally is caused by the imbalance of carbohydrates, lipids, proteins, vitamins, electrolytes, water, and the like. Examples of the metabolic diseases include obesity, diabetes, hyperlipidemia, arteriosclerosis, hypertension, and the like. Among these, type 2 diabetes which is adult-onset diabetes is characterized by an increase in insulin resistance. When the number of insulin receptors decreases, the sensitivity of insulin receptors lowers, or a problem of a second messenger that activates intracellular glycogenesis arises, sensitivity to insulin lowers. Therefore, type 2 diabetes which is referred to as non-insulin dependent diabetes accounts for 85 to 90% of diabetes.

Meanwhile, in recent years, it has been reported that a prokaryotic cell or a eukaryotic cell secretes extracellular vesicles and the secreted vesicles perform various functions. Extracellular vesicles secreted from bacteria are known to contain a lipopolysaccharide (LPS) and bacteria-derived proteins, and to induce an inflammatory disease. However, a mechanism of inhibiting the local inflammatory response caused by pathogenic bacteria-derived vesicles is not known yet.

In addition, it has been reported that extracellular vesicles are found in various secreted substances, excreta, or tissue lavage fluid from humans or animals, and that extracellular vesicles present in tissue are known to reflect a state of the tissue that secretes the vesicles, and can be used to diagnose a disease.

In the large intestine, gut microbiota is present in a number about 10 times the number of host cells. *Akkermansia muciniphila* is known as a mucin-degrading Gram-negative bacterium that lives in the large intestine of mammals including humans in symbiosis, and is associated with diabetes and obesity. Also, it has been known that *Akkermansia muciniphila* itself aggravates an inflammatory bowel disease. In recent years, the present inventors have reported that *Akkermansia muciniphila* secretes extracellular vesicles, which are able to prevent an inflammatory bowel disease (Kang C S et al., Extracellular vesicles derived from Gut microbiota, especially *Akkermansia muciniphila*, protect the progression of dextran sulfate sodium-induced colitis; PLOS ONE 2013).

Meanwhile, 5' AMP-activated protein kinase (AMPK) is an enzyme that plays an important role in cellular energy homeostasis, and is expressed in the liver, brain, muscle, adipose tissue, pancreas, and the like. It is known that when AMPK is activated, cholesterol synthesis and triglyceride synthesis are inhibited in the liver, fatty acid oxidation and glucose uptake are stimulated in muscle, and insulin secretion is regulated in the pancreas. Also, it is known that a metabolic disease is improved by activating AMPK through metformin, which is one of the therapeutic agents for diabetes, for recovering insulin resistance, or exercise, etc.

However, there is no research finding that shows a metabolic disease such as obesity or diabetes, etc. can be alleviated or treated by *Akkermansia muciniphila*-derived extracellular vesicles, not by *Akkermansia muciniphila* itself.

DISCLOSURE

Technical Problem

The present inventors found that extracellular vesicles secreted from *Akkermansia muciniphila* inhibit obesity and diabetes induced by a high fat diet, and recover insulin resistance which is important to an etiological cause of diabetes caused by a high fat diet, all of which occur when AMPK is activated. Therefore, the present invention was completed based on this fact.

Therefore, an object of the present invention is to provide a pharmaceutical and food composition for treating or preventing metabolic diseases such as obesity, diabetes, hyperlipidemia, hypertension, etc., using *Akkermansia muciniphila*-derived extracellular vesicles.

Technical Solution

To achieve such an object, the present invention provides a pharmaceutical composition containing *Akkermansia muciniphila*-derived extracellular vesicles as an active ingredient for treating or preventing a metabolic disease.

In addition, the present invention provides a food composition containing *Akkermansia muciniphila*-derived extracellular vesicles for preventing or alleviating a metabolic disease.

In addition, the present invention provides a method for preventing or treating a metabolic disease, which includes administering *Akkermansia muciniphila*-derived extracellular vesicles to a subject.

In addition, the present invention provides a use of *Akkermansia muciniphila*-derived extracellular vesicles for preventing or treating a metabolic disease.

In an embodiment of the present invention, the extracellular vesicles may be naturally or artificially secreted from *Akkermansia muciniphila*.

In another embodiment of the present invention, the extracellular vesicles may have an average diameter of 20 to 300 nm, and preferably, 50 to 200 nm.

In still another embodiment of the present invention, the metabolic disease may be selected from the group consisting of obesity, diabetes, hyperlipidemia, and hypertension.

In yet another embodiment of the present invention, the food may be a fermented food prepared through fermentation by adding *Akkermansia muciniphila*.

Advantageous Effects

A pharmaceutical composition according to the present invention, which contains *Akkermansia muciniphila*-derived extracellular vesicles as an active ingredient, can treat and prevent metabolic diseases such as obesity, diabetes, hyperlipidemia, hypertension, etc., which are induced by a high fat diet.

In addition, a fermented food composition according to the present invention, which contains *Akkermansia muciniphila*-derived extracellular vesicles, can prevent and alleviate metabolic diseases such as obesity, diabetes, hyperlipidemia, hypertension, etc., which are induced by a high fat diet.

MODES OF THE INVENTION

Figure 1:
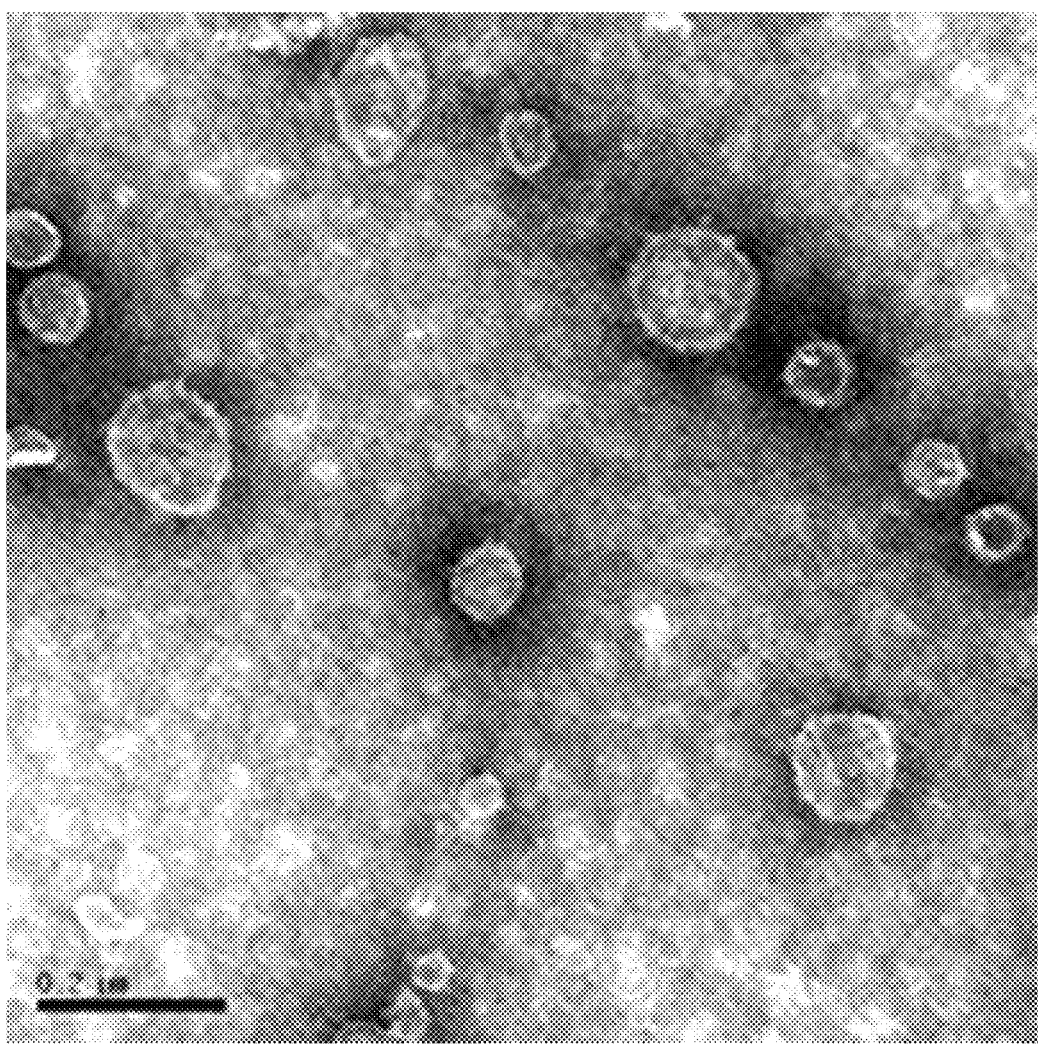
FIG. 1 illustrates a result obtained by observing extracellular vesicles isolated from a culture medium of *Akkermansia muciniphila* through an electron microscope.

The present invention relates to a pharmaceutical/food composition containing extracellular vesicles derived from enteric bacteria, particularly *Akkermansia muciniphila*, as an active ingredient for treating, preventing or alleviating a metabolic disease.

The present inventors have found that when *Akkermansia muciniphila*-derived extracellular vesicles (EV) are administered to the stomach of metabolic disease mouse models induced by a high fat diet, obesity is inhibited, insulin resistance induced by a fatty acid is recovered, the diabetes phenotype is inhibited, and an immune function is enhanced.

In addition, the present inventors have found that protein expression patterns of *Akkermansia muciniphila* itself and an *Akkermansia muciniphila*-derived extracellular vesicle are different from each other.

In addition, the present inventors have found, through a result obtained by comparing in vivo absorption patterns of *Akkermansia muciniphila* itself and an *Akkermansia muciniphila*-derived extracellular vesicle, that the in vivo absorption of extracellular vesicles is remarkably superior.

In addition, the present inventors have found that when *Akkermansia muciniphila*-derived extracellular vesicles are administered to myocytes, expression of a glucose uptake receptor (GLUT4) in myocytes is promoted by AMPK activation, thereby increasing glucose uptake.

In this specification, a "metabolic disease" refers to a general term for diseases that occur due to an in vivo metabolic disorder. The metabolic disease is generally caused by the imbalance of carbohydrates, lipids, proteins, vitamins, electrolytes, water, and the like. Representative examples thereof include obesity, diabetes, hyperlipidemia, arteriosclerosis, and the like, all of which are caused by a high fat diet.

In this specification, "treating or preventing a metabolic disease" includes alleviating and mitigating a metabolic disease, and improving symptoms, and also, includes lowering the probability of getting a metabolic disease.

In this specification, an "*Akkermansia muciniphila*-derived extracellular vesicle" may be isolated from a culture medium of *Akkermansia muciniphila* or a food fermented with *Akkermansia muciniphila*. A method for isolating the extracellular vesicle from the culture medium of *Akkermansia muciniphila* or the food fermented with *Akkermansia muciniphila* is not specifically limited as long as extracellular vesicles are included. For example, extracellular vesicles may be isolated from a bacteria culture medium or a fermented food using a method such as centrifugation, ultracentrifugation, filtration with a filter, gel filtration chromatography, free-flow electrophoresis, capillary electrophoresis, isolation using a polymer, or a combination thereof. In addition, processes such as washing for removing impurities and concentration of obtained extracellular vesicles may be further included.

The extracellular vesicles include extracellular vesicles naturally or artificially secreted.

The extracellular vesicles isolated by the method may have an average diameter of 20 to 300 nm, and preferably, 30 to 200 nm.

In an embodiment of the present invention, the composition for treating or preventing a metabolic disease may be prepared into a pharmaceutical composition. In order to use the composition for treatment and prevention, it is possible to administer extracellular vesicles according to the present invention themselves, but it is preferable that the pharmaceutical composition contains the extracellular vesicles as an active ingredient.

The pharmaceutical composition contains the isolated extracellular vesicles as an active ingredient and may include a pharmaceutically acceptable carrier. The pharmaceutically acceptable carrier that can generally be used in formulation includes saline, sterile water, Ringer's solution, buffered saline, cyclodextrins, a dextrose solution, a maltodextrin solution, glycerol, ethanol, a liposome, and the like, but the present invention is not limited thereto. As necessary, other conventional additives such as an antioxidant, a buffer, etc. may be further included. Also, a diluent, a dispersant, a surfactant, a binder, a lubricant, and the like may be further added to prepare the composition into an injectable formulation such as an aqueous solution, a suspension, an emulsion, etc., a pill, a capsule, a granule, or a tablet. A suitable pharmaceutically acceptable carrier and a preparation thereof may be preferably referenced from the method disclosed in the Remington's document (Remington's Pharmaceutical Science, Mack Publishing Company, Easton Pa.) according to a component. The pharmaceutical composition according to the present invention is not limited to a formulation, but may be prepared into injections, inhalations, skin remedies for external use, and the like.

A method for administering a pharmaceutical composition according to the present invention is not specifically limited, but may include parenteral administration such as intravenous administration, subcutaneous administration, intraperitoneal administration, inhalation, dermal application, or topical application, or oral administration depending on a desired method.

A dose range may vary depending on weight, age, gender, and health condition of a patient, a diet, the duration of administration, an administration mode, an excretion rate, severity of disease, and the like. A dose used daily refers to a sufficient amount of the therapeutic substance of the present invention, which is administered to a subject requiring treatment so as to alleviate a disease. An effective dose of the therapeutic substance may vary depending on a specific compound, the state and severity of a disease, and a subject that requires treatment and may be generally determined by skilled practitioners. As a non-limiting example, a dose of the composition according to the present invention for a human body may vary depending on age, weight, and gender of a patient, an administration mode, health condition, and the severity of disease. In the case of an adult patient having a weight of 70 kg, the composition may be generally administered at a dose of 0.01 to 1000 mg/day, and preferably, 1 to 500 mg/day. In this case, divided administration may be performed at a predetermined time interval once or several times a day.

In an embodiment of the present invention, the composition for preventing or alleviating a metabolic disease may be prepared into a food composition. When the composition according to the present invention is prepared into a food composition, the food composition may include the extracellular vesicles as an active ingredient, and also include ingredients that are generally added in food production, for example, proteins, carbohydrates, lipids, nutrients, a seasoning agent, and a flavoring agent. For example, when the food composition according to the present invention is prepared into drinks, citric acid, high fructose corn syrup, sugar, glucose, acetic acid, malic acid, fruit juice, and the like in addition to extracellular vesicles according to the present invention may be further included.

When the composition according to the present invention is prepared into a food composition, a fermented food such as kimchi on its own may be used.

Hereinafter, exemplary examples of the invention will be described for promoting understanding of the present invention. However, the following examples should be considered in a descriptive sense only, and the scope of the invention is not limited to the examples.

EXAMPLE 1

Isolation of Extracellular Vesicles from Culture Medium of *Akkermansia muciniphila*

An *Akkermansia muciniphila* strain (ATCC BAA-835) was cultured in 2 L of autoclaved Brain-heart infusion broth (BD 237500) in an anaerobic chamber for 72 hours so that an O.D value became 1.5, and then a culture medium was centrifuged at a high speed (10,000×g) for 20 minutes to obtain a supernatant excluding a precipitated bacterial cell pellet. The supernatant was filtered with a 0.45 μm filter and a 0.22 μm filter, thus obtaining a culture medium concentrated about 14 fold using the Quixstand benchtop system. The culture medium was ultracentrifuged (150,000×g) at 4° C. for 2 hours to obtain pellets, and then the pellets was dissolved with sterile saline (PBS), followed by protein quantification.

EXAMPLE 2

Characteristic Analysis of Extracellular Vesicles

In order to confirm whether the substance obtained by the method of Example 1 is *Akkermansia muciniphila*-derived extracellular vesicles, a 50 μg/ml sample obtained by quantifying proteins was observed through the JEM 1011 electron microscope (commercially available from Jeol Ltd., Japan). As a result, as shown in FIG. 1, it can be seen that the *Akkermansia muciniphila*-derived extracellular vesicle is spherical.

Figure 2:
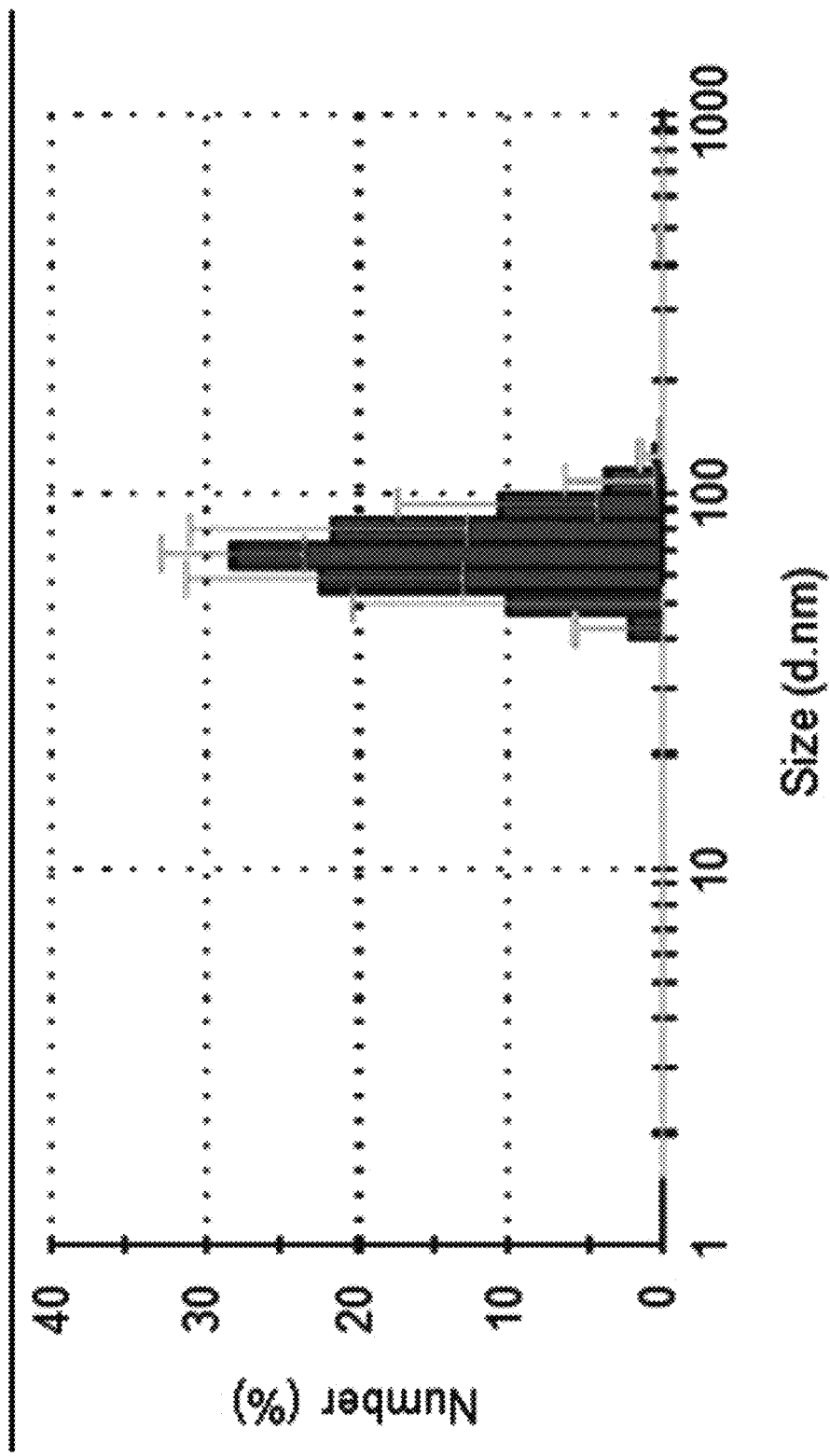
FIG. 2 illustrates a result obtained by measuring an average diameter of *Akkermansia muciniphila*-derived extracellular vesicles through a light scattering method.

In addition, in order to confirm a size of an extracellular vesicle isolated from *Akkermansia muciniphila* using a dynamic light scattering (DLS) method, a 50 μg/ml sample was measured through the Zetasizer Nano ZS (commercially available from Malvem Instruments Ltd, UK). As a result, as shown in FIG. 2, it can be seen that *Akkermansia muciniphila*-derived extracellular vesicles have an average diameter of 20 to 300 nm.

Figure 3:
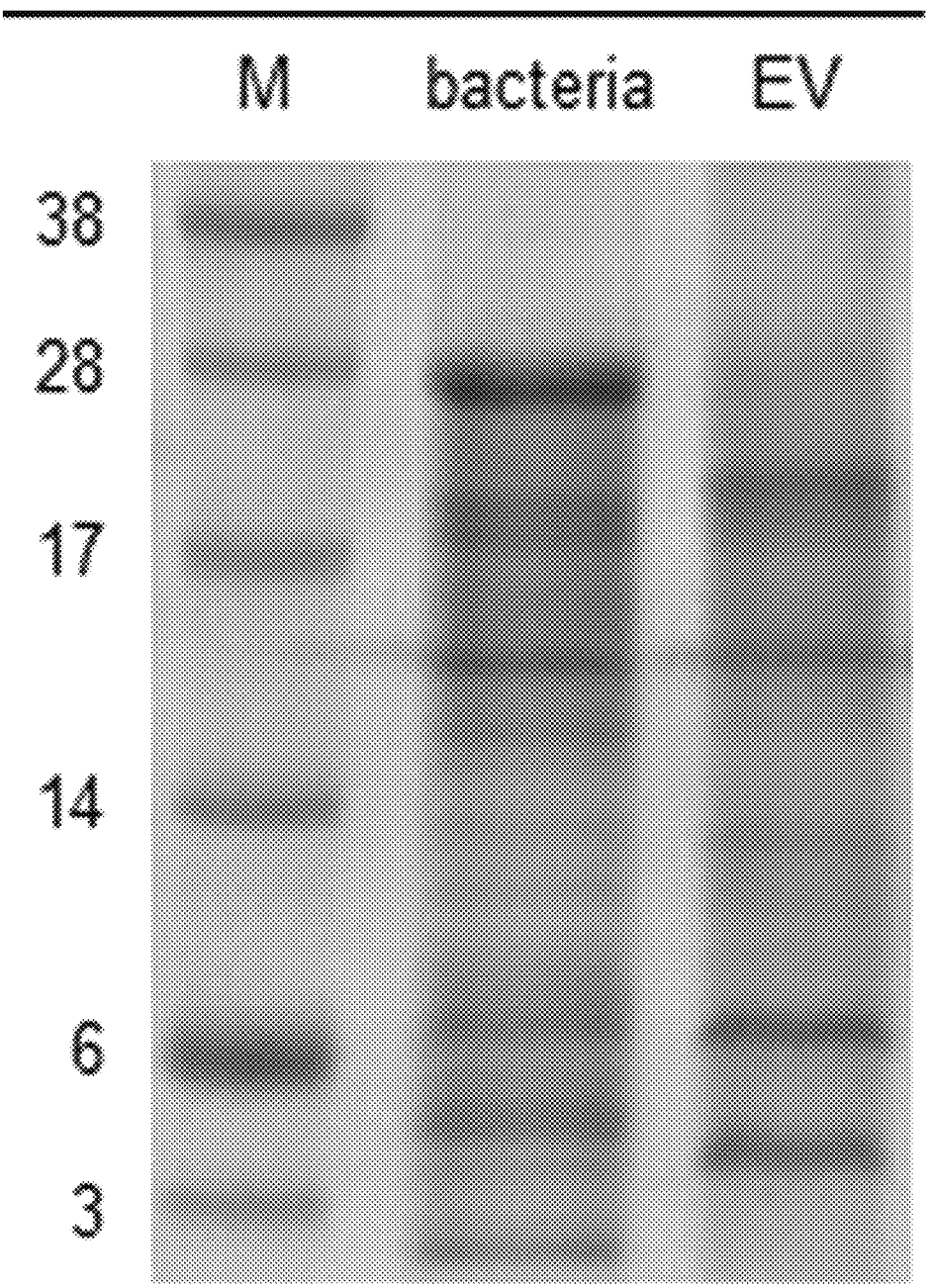
FIG. 3 illustrates a result obtained by comparing and evaluating protein expression patterns of *Akkermansia muciniphila* and *Akkermansia muciniphila*-derived extracellular vesicles through SDS-PAGE.

In addition, in order to confirm a protein expression pattern of extracellular vesicles isolated from *Akkermansia muciniphila*, a 10 μg/ml sample was assessed by SDS-PAGE. As a result, as shown in FIG. 3, it can be seen that the protein expression pattern of *Akkermansia muciniphila*-derived extracellular vesicles (EV) is different from that of *Akkermansia muciniphila* (bacteria).

Figure 4:
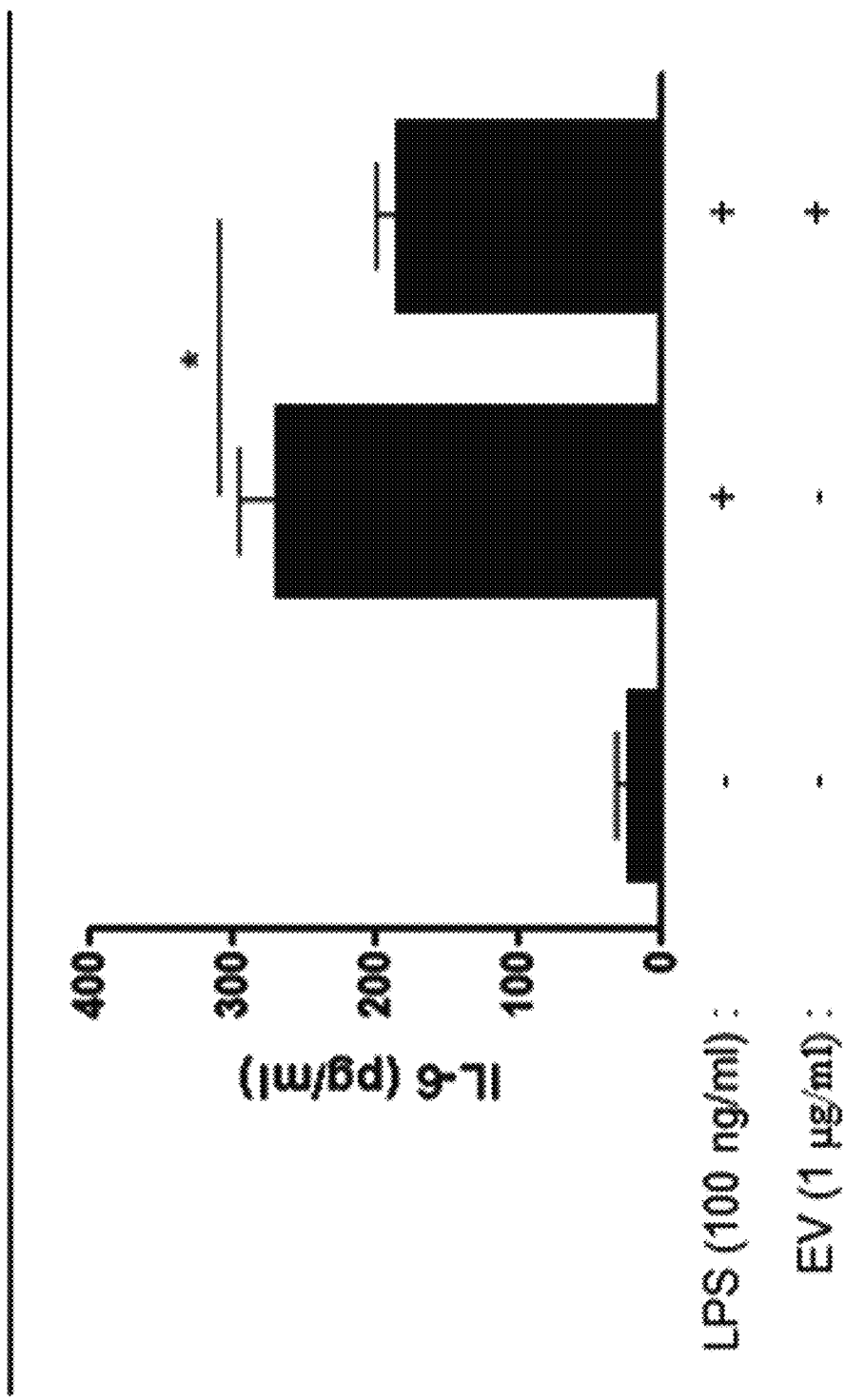
FIG. 4 illustrates a result showing that secretion of pro-inflammatory cytokines (IL-6) caused by LPS is inhibited when a macrophage is pretreated with *Akkermansia muciniphila*-derived extracellular vesicles (EV).

In addition, in order to evaluate an anti-inflammatory effect of extracellular vesicles isolated from *Akkermansia muciniphila*, secreted pro-inflammatory cytokines were assessed by enzyme-linked immunosorbent assay (ELISA) after macrophages had been pretreated with extracellular vesicles (1 μg/ml) before treatment with LPS (100 ng/ml). As a result, as shown in FIG. 4, it can be seen that when the macrophages are pretreated with *Akkermansia muciniphila*-derived extracellular vesicles, an amount of IL-6 secreted by LPS decreases.

EXAMPLE 3

Therapeutic Effects of *Akkermansia muciniphila*-Derived Extracellular Vesicles in Obese and Diabetic Mouse Induced by a High Fat Diet In order to confirm whether the *Akkermansia muciniphila*-derived extracellular vesicles obtained in Example 1 inhibit obesity and diabetes induced by a high fat diet, an experiment was performed as follows.

Figure 5:
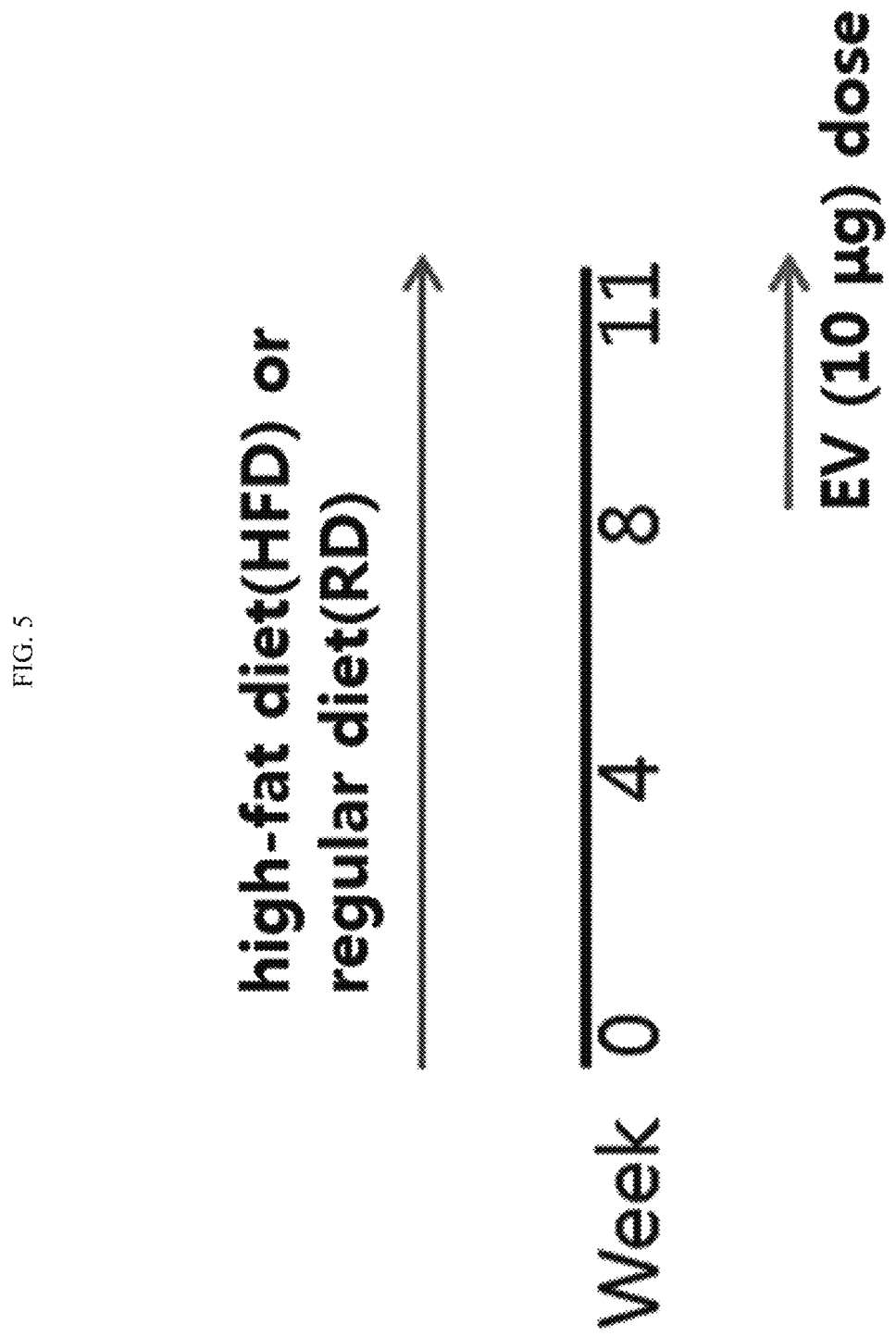
FIG. 5 illustrates an experimental protocol for confirming a therapeutic effect on a metabolic disease after *Akkermansia muciniphila*-derived extracellular vesicles (EV) are directly administered to the stomach of obese and diabetic mouse models induced by a high fat diet.

The extracellular vesicles obtained in Example 1 were administered to each of normal mice which were fed a regular diet (RD) for 2 months and obese and diabetic mouse models induced by being fed a high fat diet (HFD) for 2 months at a dose of 10 μg/mouse for 3 weeks at two day intervals (See FIG. 5). In this case, a group of only RD-fed mice and a group of RD-fed and extracellular vesicle-administered mice were used as negative controls.

Figure 6:
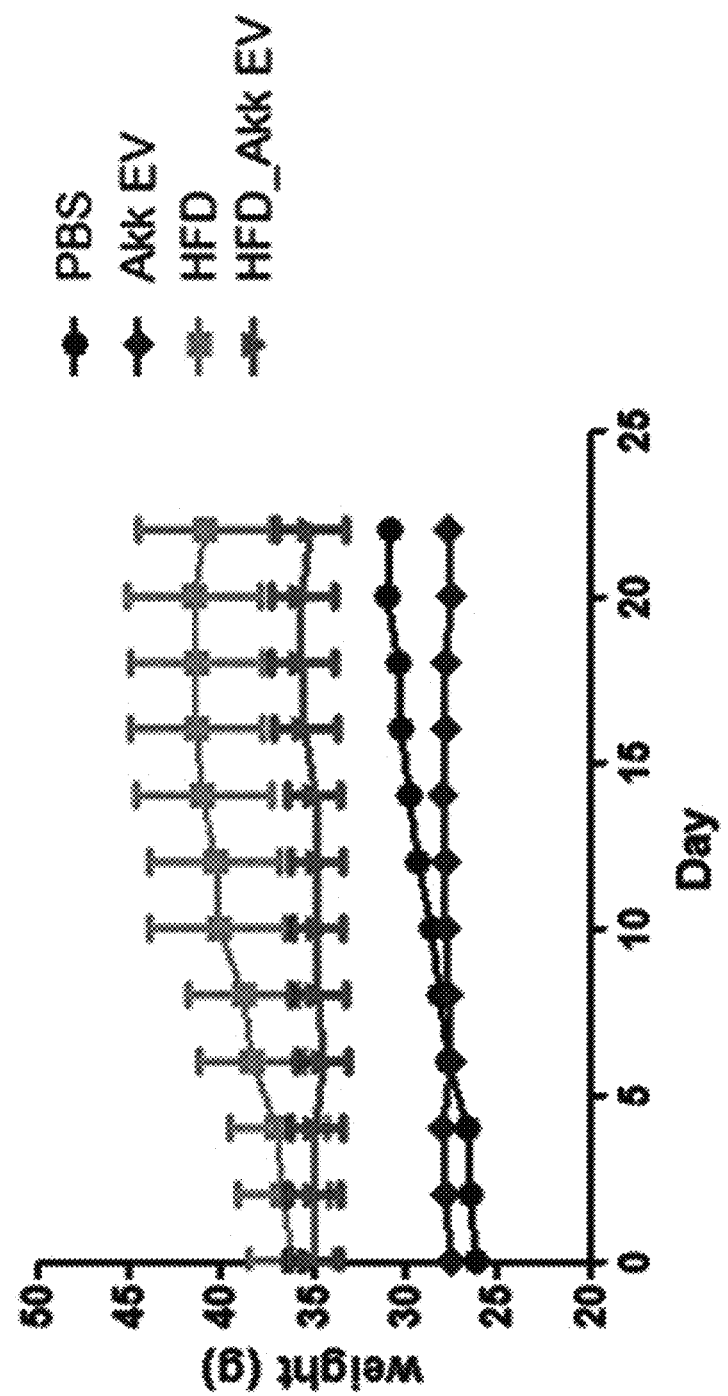
FIG. 6 illustrates a result obtained by observing a change in weight after *Akkermansia muciniphila*-derived extracellular vesicles (Akk EV) are directly administered to the stomach of metabolic disease mouse models induced by a high fat diet.

In a result obtained by measuring weight while extracellular vesicles are administered at two day intervals, as shown in FIG. 6, it can be seen that a weight was not increased for 3 weeks in a HFD-fed, extracellular vesicle-administered mouse group (HFD_Akk EV), compared to an only HFD-fed mouse group (HFD).

Figure 7:
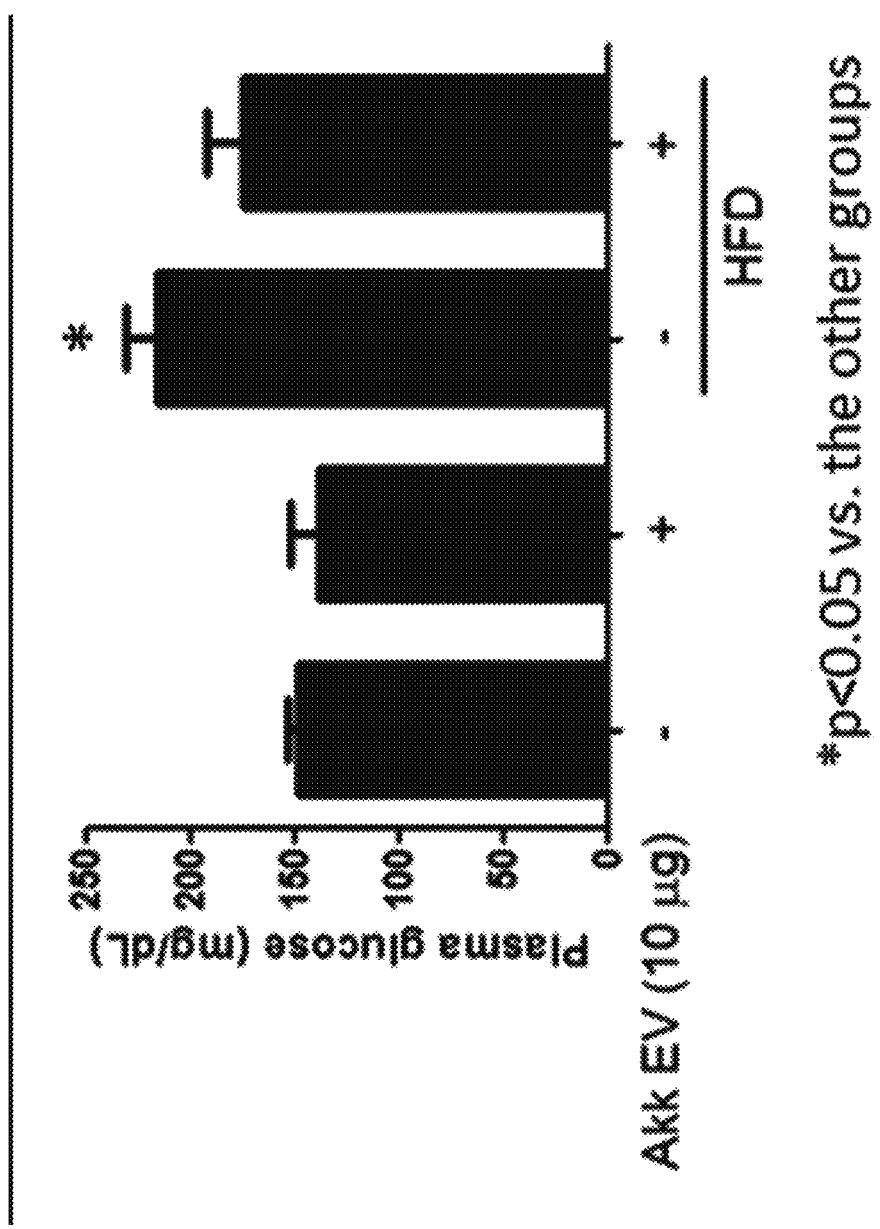
FIG. 7 illustrates a result obtained by measuring a plasma glucose level when fasting after *Akkermansia muciniphila*-derived extracellular vesicles (Akk EV) are directly administered to the stomach of metabolic disease mouse models induced by a high fat diet.

In addition, in a result obtained by measuring a plasma glucose level when fasting for 6 hours after administration of extracellular vesicles was completed, as shown in FIG. 7, it can be seen that the plasma glucose level decreases in a HFD-fed, extracellular vesicle-administered mouse group (HFD+Akk EV), compared to an only HFD-fed mouse group (HFD−Akk EV).

Figure 8:
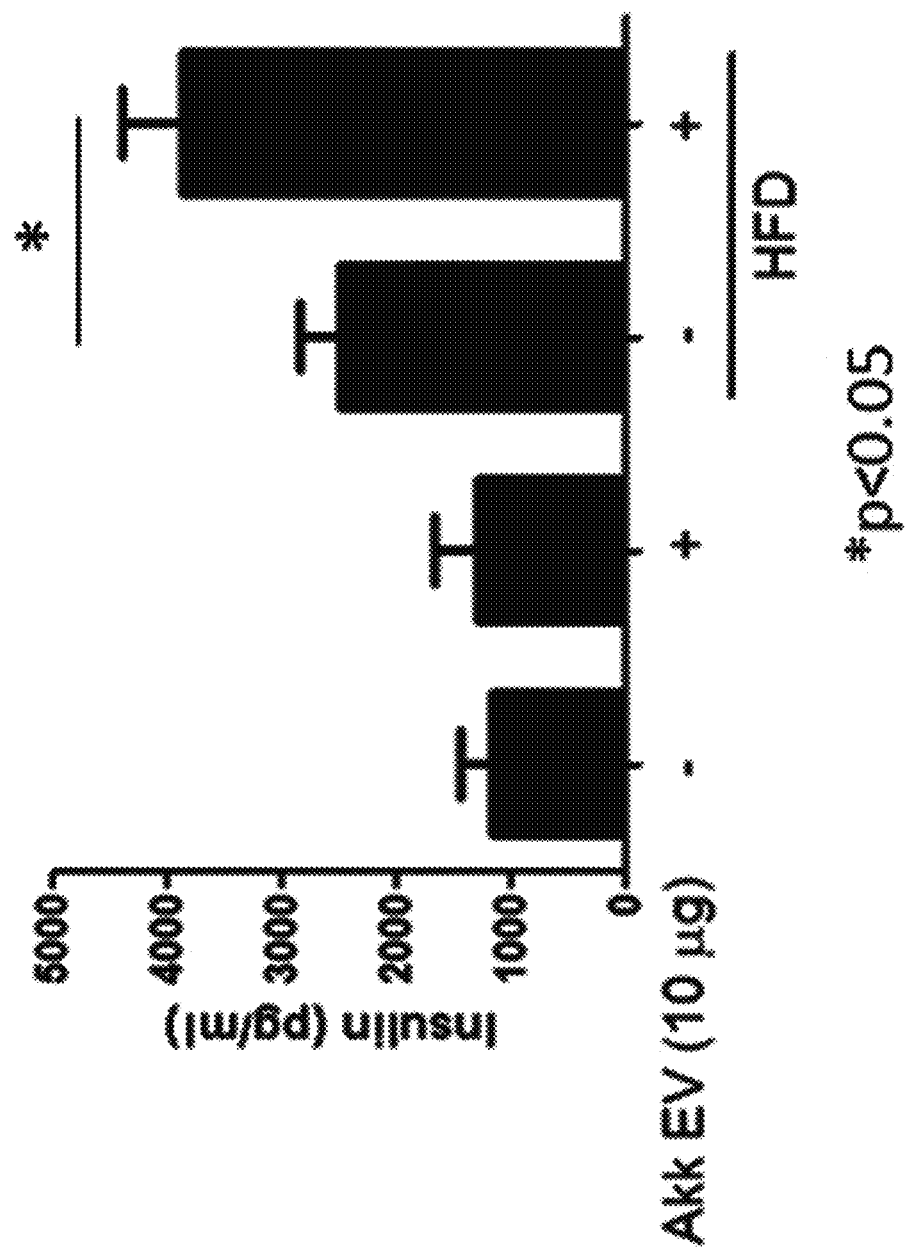
FIG. 8 illustrates a result obtained by measuring an insulin concentration in blood after *Akkermansia muciniphila*-derived extracellular vesicles (Akk EV) are directly administered to the stomach of metabolic disease mouse models induced by a high fat diet.

In addition, in a result obtained by measuring an insulin concentration in blood collected from a mouse heart 24 hours after administration of extracellular vesicles had completed, as shown in FIG. 8, it can be seen that an insulin concentration is more increased in a HFD-fed, extracellular vesicle-administered mouse group (HFD+Akk EV), compared to an only HFD-fed mouse group (HFD−Akk EV).

The result indicates that *Akkermansia muciniphila*-derived extracellular vesicles are effective in treating obesity and diabetes induced by a high fat diet.

EXAMPLE 4

Immune Function Regulatory Effect

In order to confirm whether the *Akkermansia muciniphila*-derived extracellular vesicles obtained in Example 1 affect an immune function, an experiment was performed as follows.

Both blood and spleen were collected from mice 24 hours after administration of extracellular vesicles had completed in the same manner as in Example 3. Immunocytes were extracted from tissues of spleen collected from respective mouse groups using 100 μm and 40 μm cell strainers. An extract was centrifuged (400×g) for 5 minutes and then counted cells were plated at $5 \times 10^5$ cells/well onto a cell culture plate. Thereafter, anti-CD3 and anti-CD28, which stimulate co-stimulatory molecules of T cells (cytokine secretion), were added to the plate at concentrations of 1 μg/mL and 0.5 μg/mL, respectively, and then cells were cultured for 48 hours.

Figure 9:
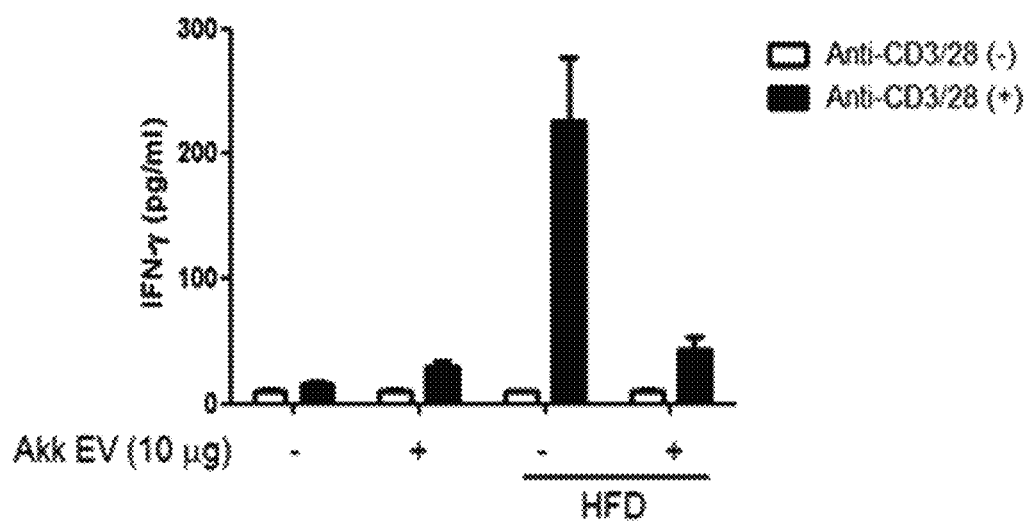
FIG. 9 illustrates a result obtained by measuring concentrations of IFN-$\gamma$ and IL-17 in supernatant liquid obtained by isolating splenocytes from the body and then stimulating with an anti-CD3 antibody and an anti-CD28 antibody for 48 hours after *Akkermansia muciniphila*-derived extracellular vesicles (Akk EV) are directly administered to the stomach of metabolic disease mouse models induced by a high fat diet.
Figure 9:
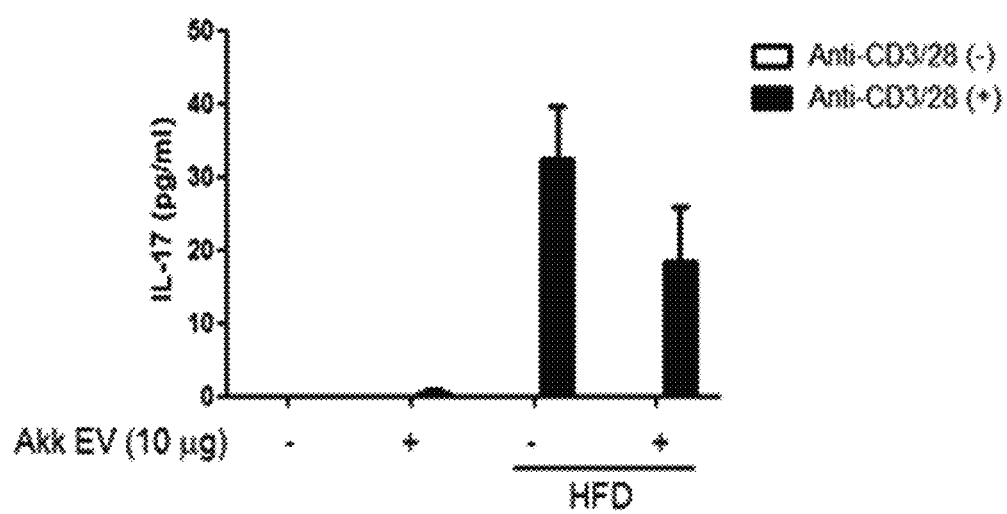

In order to confirm a secretion difference of pro-inflammatory cytokines among respective groups after culture is completed, supernatants of respective groups collected from the cell culture plate were centrifuged (400×g) for 5 minutes to remove cells present in the supernatants, and then only supernatants were collected again. In a result obtained by confirming concentrations of IFN-γ and IL-17 in the collected supernatants through ELISA, as shown in FIG. 9, it can be seen that while concentrations of IFN-γ and IL-17 increase in an only HFD-fed mouse group (HFD−Akk EV), concentrations of IFN-γ and IL-17 decrease in a HFD-fed mouse group to which *Akkermansia muciniphila*-derived extracellular vesicles were administered (HFD+Akk EV).

A decrease in pro-inflammatory cytokines such as IFN-γ and IL-17 indicates that it is possible to treat obesity and diabetes by improving an immune function because obesity and diabetes are related to inflammation.

EXAMPLE 5

Influence of Insulin Resistance on Inhibition of Signal Transduction

In order to confirm whether the *Akkermansia muciniphila*-derived extracellular vesicles obtained in Example 1 recover insulin resistance, an experiment was performed as follows.

In order to implement insulin resistance in vitro, a culture medium of mouse-derived myocytes (C2C12, ATCC CRL-1772) was treated with a 1 mM fatty acid (sodium palmitate, SIGMA) and 4% bovine serum albumin (BSA) for 48 hours. Thereafter, *Akkermansia muciniphila*-derived extracellular vesicles were added at a concentration of 1 µg/ml to the treated culture medium, cultured for 6 hours, and then treated with 2 nM insulin to confirm intracellular signal transduction.

Figure 10:
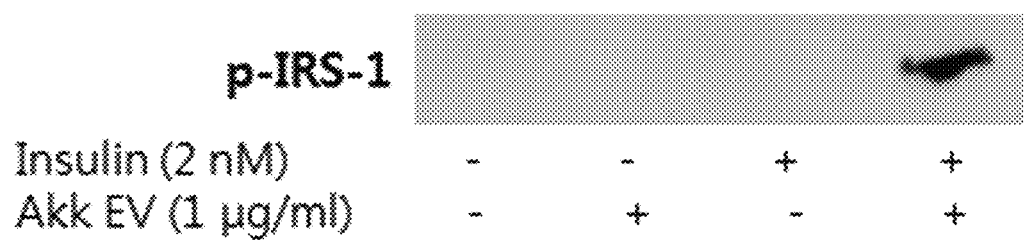
FIG. 10 illustrates a result obtained by confirming whether inhibited insulin signal transduction is recovered by *Akkermansia muciniphila*-derived extracellular vesicles (Akk EV) after mouse myocytes are treated with high fatty acids to induce insulin resistance.

In a result obtained by confirming, by the western blot, a difference in an amount of phospho-insulin receptor substrate-1 (p-IRS-1) used as an important indicator in intracellular insulin signal transduction between a group which was not treated with insulin and a group which was treated with insulin, as shown in FIG. 10, it can be seen that p-IRS-1 was observed in an extracellular vesicle-treated group, which indicates that intracellular signal transduction inhibited by insulin resistance was recovered.

The result indicates that *Akkermansia muciniphila*-derived extracellular vesicles can play a role in recovering insulin resistance induced by high fatty acids in myocytes, that is, inhibition of intracellular signal transduction by insulin.

EXAMPLE 6

In Vivo Absorption, Distribution, and Excretion Patterns of Bacteria and Bacteria-Derived Extracellular Vesicles In order to compare and evaluate whether *Akkermansia muciniphila* and *Akkermansia muciniphila*-derived extracellular vesicles are systemically absorbed through the gastrointestinal tract, an experiment was performed as follows.

Figure 11:
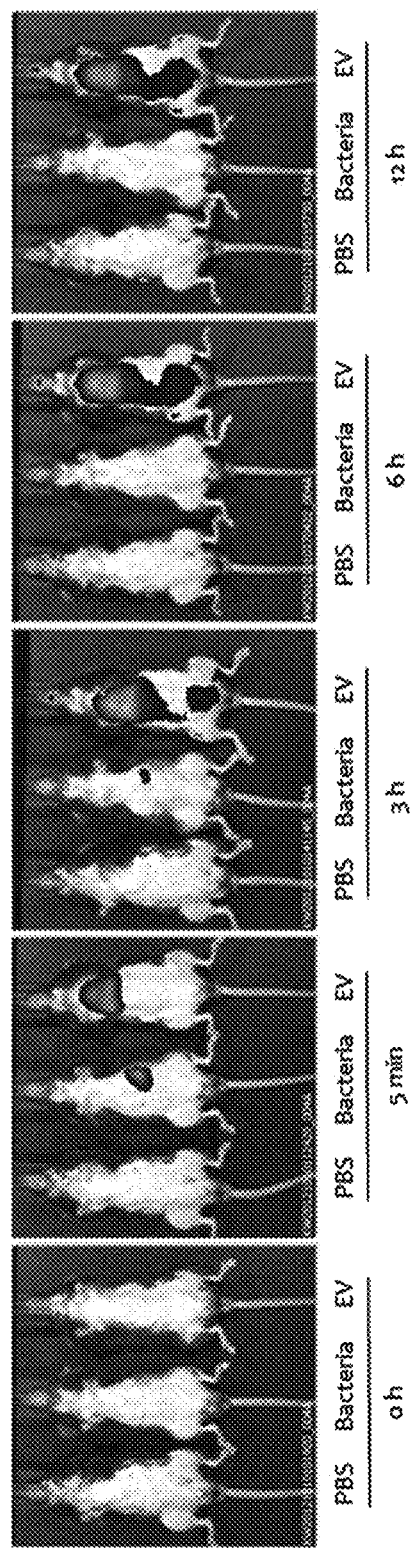
FIG. 11 illustrates a result obtained by comparing and evaluating in vivo distribution patterns of *Akkermansia muciniphila* (bacteria) and *Akkermansia muciniphila*-derived extracellular vesicles (EV) after each of *Akkermansia muciniphila* (bacteria) and *Akkermansia muciniphila*-derived extracellular vesicles (EV) are directly administered to a mouse's stomach.

First, PBS was used as a control group. Each of *Akkermansia muciniphila* and *Akkermansia muciniphila*-derived extracellular vesicles, which were labeled with fluorescence, were administered to a mouse gastrointestinal tract at a dose of 50 µg, and then fluorescence was measured using a fluorescence and bioluminescence imaging system (In vivo imaging system (IVIS)) after 0 minute, 5 minutes, 3 hours, 6 hours, and 12 hours had elapsed. As a result, as shown in FIG. 11, it can be seen that the bacteria were not absorbed systemically, but the bacteria-derived extracellular vesicles were absorbed systemically in just 5 minutes after administration, excreted through urinary organs, which was seen from strong fluorescence in the bladder at 3 hours after administration, and present in the body even at 12 hours after administration.

Figure 12:
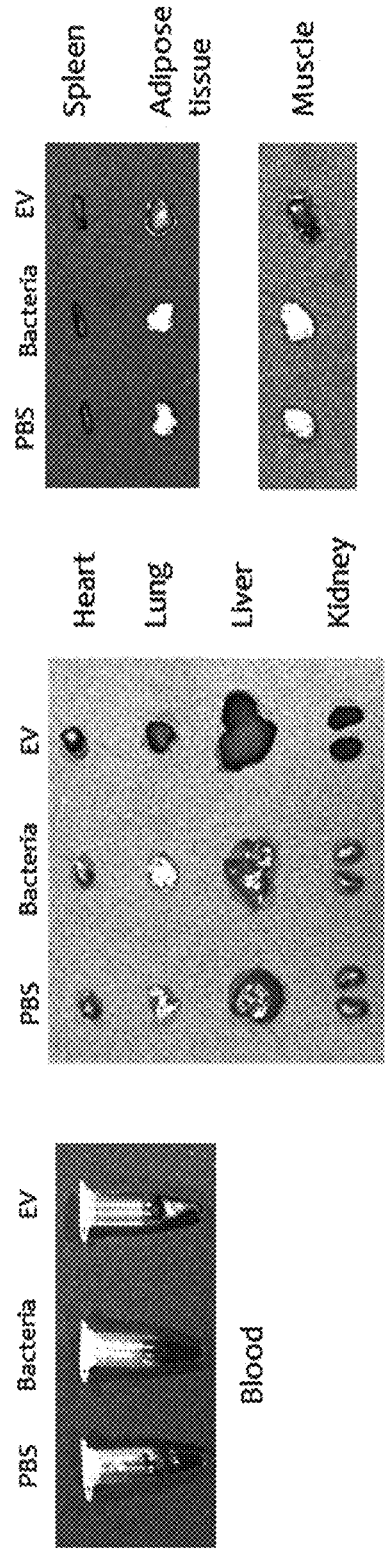
FIG. 12 illustrates a result obtained by comparing and evaluating in vivo distribution patterns of *Akkermansia muciniphila* (bacteria) and *Akkermansia muciniphila*-derived extracellular vesicles (EV) by extracting blood and various organs (such as heart, lungs, liver, kidney, spleen, adipose tissue, and muscle) at 12 hours after each of *Akkermansia muciniphila* (bacteria) and *Akkermansia muciniphila*-derived extracellular vesicles (EV) are directly administered to a mouse's stomach.

In addition, in order to confirm a pattern in which extracellular vesicles are infiltrated into various organs after *Akkermansia muciniphila*-derived extracellular vesicles are systemically absorbed, blood, heart, lungs, liver, kidney, spleen, adipose tissue, and muscle samples were extracted at 12 hours after fluorescence-labeled extracellular vesicles had been administered to a mouse's gastrointestinal tract at a dose of 50 µg. In a result obtained by observing fluorescence in the extracted tissue samples by IVIS, as shown in FIG. 12, it can be seen that the extracellular vesicles are distributed in all of the blood and organ samples at 12 hours after the extracellular vesicles have been administered to the gastrointestinal tract. But fluorescence of the bacterium itself was not observed.

Figure 13:
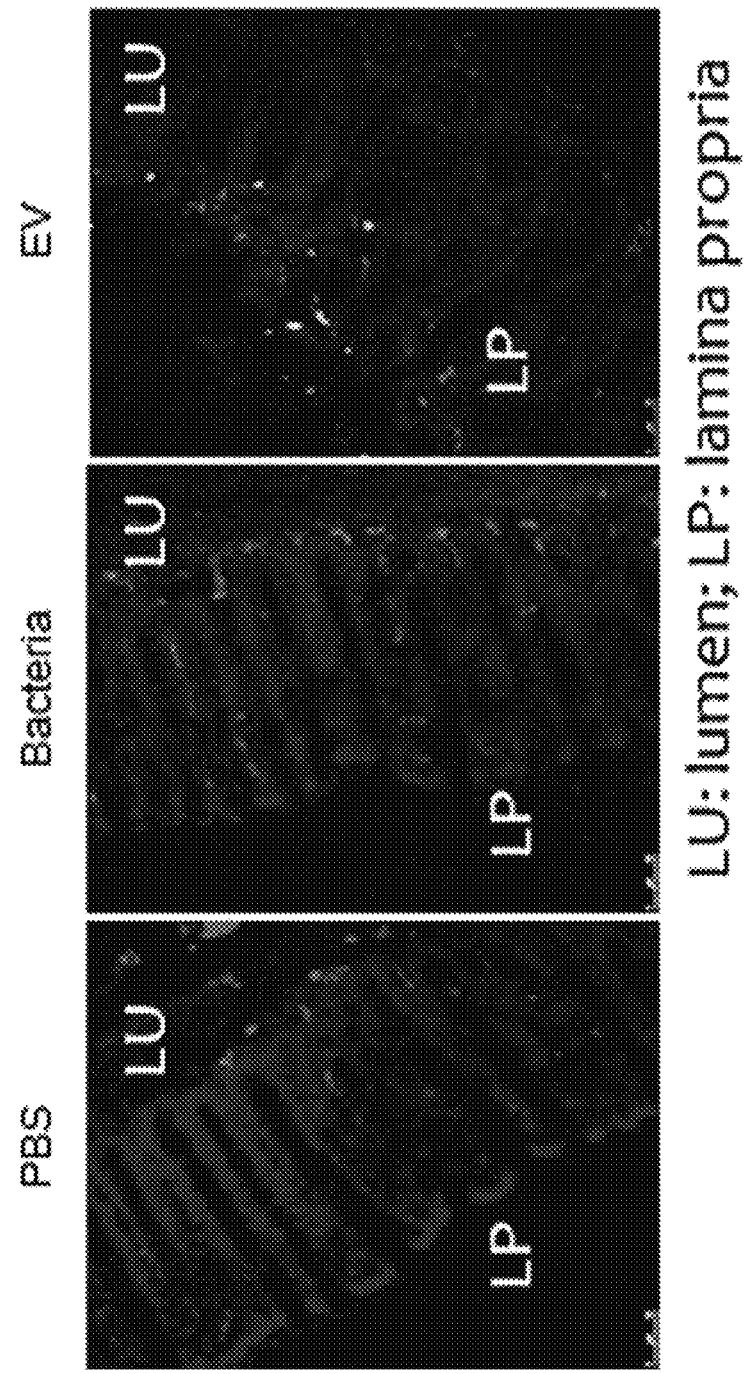
FIG. 13 illustrates a result obtained by comparing and evaluating whether *Akkermansia muciniphila* (bacteria) and *Akkermansia muciniphila*-derived extracellular vesicles (EV) penetrate an intestinal barrier and then are absorbed into tissue after each of *Akkermansia muciniphila* (bacteria) and *Akkermansia muciniphila*-derived extracellular vesicles (EV) are directly administered to a mouse's large intestine.

In addition, in order to confirm whether *Akkermansia muciniphila*-derived extracellular vesicles penetrate an intestinal barrier, each of *Akkermansia muciniphila* bacteria and *Akkermansia muciniphila*-derived extracellular vesicles were administered to a mouse's large intestine at a dose of 10 µg for 10 minutes. In a result obtained by checking the isolated large intestine by immunohistochemistry (IHC), as shown in FIG. 13, it can be seen that the bacteria do not penetrate an intestinal barrier, but the extracellular vesicles penetrate an intestinal barrier to be absorbed into the tissue.

Figure 14:
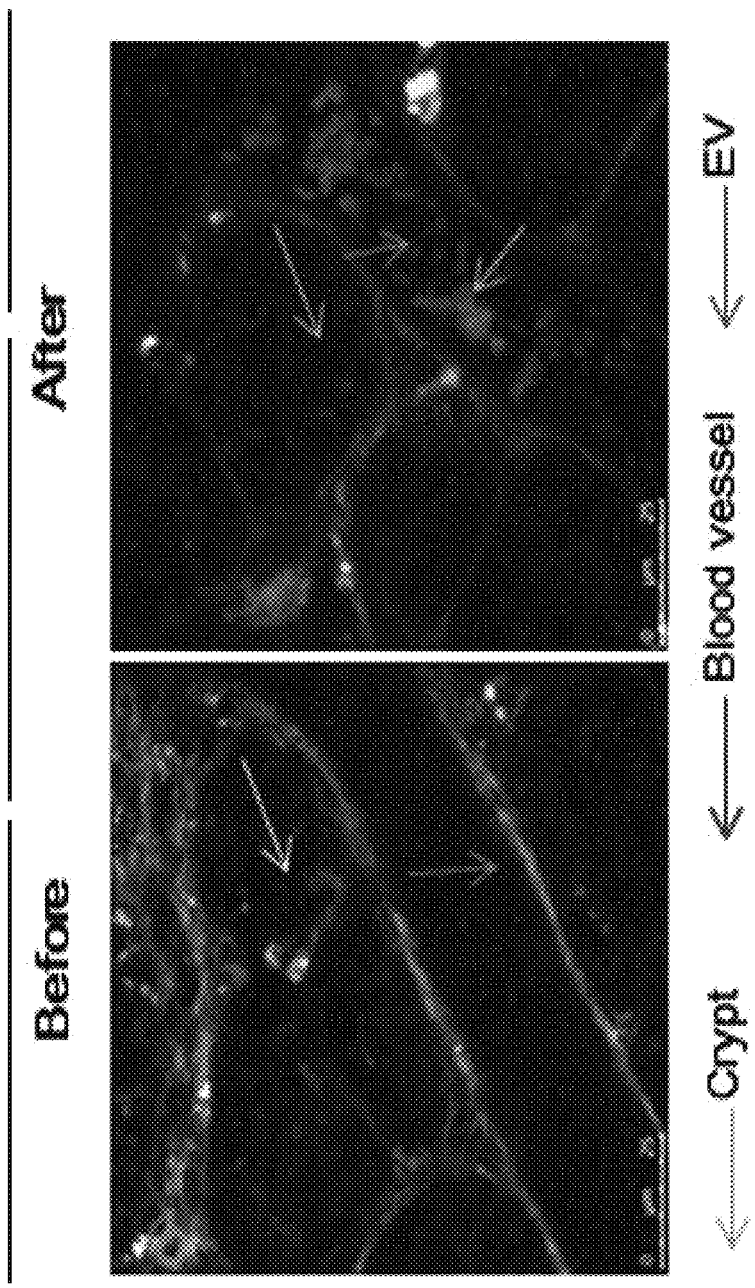
FIG. 14 illustrates a result obtained by confirming whether extracellular vesicles are absorbed into intestinal capillaries after *Akkermansia muciniphila*-derived extracellular vesicles (EV) are directly administered to a mouse's large intestine.

In addition, in order to confirm whether *Akkermansia muciniphila*-derived extracellular vesicles penetrate an intestinal barrier to be absorbed into intestinal capillaries, fluorescence-labeled extracellular vesicles were administered to a mouse's large intestine at a dose of 10 µg. In a result obtained by observing intestinal capillaries by a live imaging method, as shown in FIG. 14, it can be seen that the extracellular vesicles are absorbed into blood vessels to migrate in blood vessels.

EXAMPLE 7

Influence of *Akkermansia muciniphila*-Derived Extracellular Vesicles on AMPK Activation in Myocytes In order to evaluate an influence of *Akkermansia muciniphila*-derived extracellular vesicles on glucose metabolism by AMPK activation in myocytes, because AMPK is known as a protein that plays an important role in maintaining energy homeostasis, an experiment was performed as follows.

Figure 15:
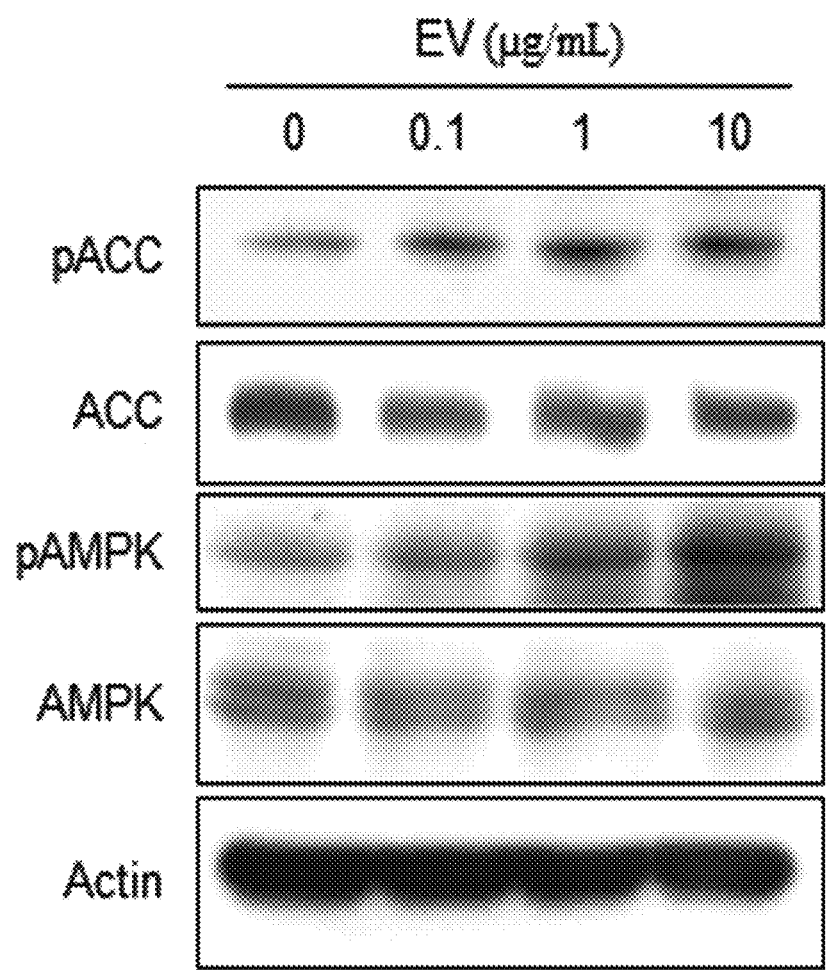
FIG. 15 illustrates a result obtained by confirming AMPK activation at 60 minutes after *Akkermansia muciniphila*-derived extracellular vesicles (EV) are administered to myocytes in vitro at varying concentrations (0.1, 1, and 10 µg/mL).

First, in order to evaluate AMPK activation based on a concentration at which treatment with *Akkermansia muciniphila*-derived extracellular vesicles is performed in vitro, myocytes were treated with extracellular vesicles at concentrations of 0, 0.1, 1, and 10 µg/ml for 1 hour. In a result obtained by measuring, by the western blot, a difference in expression levels of phospho-5' AMP-activated protein kinase (pAMPK) and phospho-acetyl-CoA carboxylase (pACC), which are used as an important indicator in AMPK signal transduction, as shown in FIG. 15, expression of pAMPK and pACC increases according to a concentration of the extracellular vesicles treated, and thus it can be seen that AMPK is activated depending on a concentration of extracellular vesicles.

Figure 16:
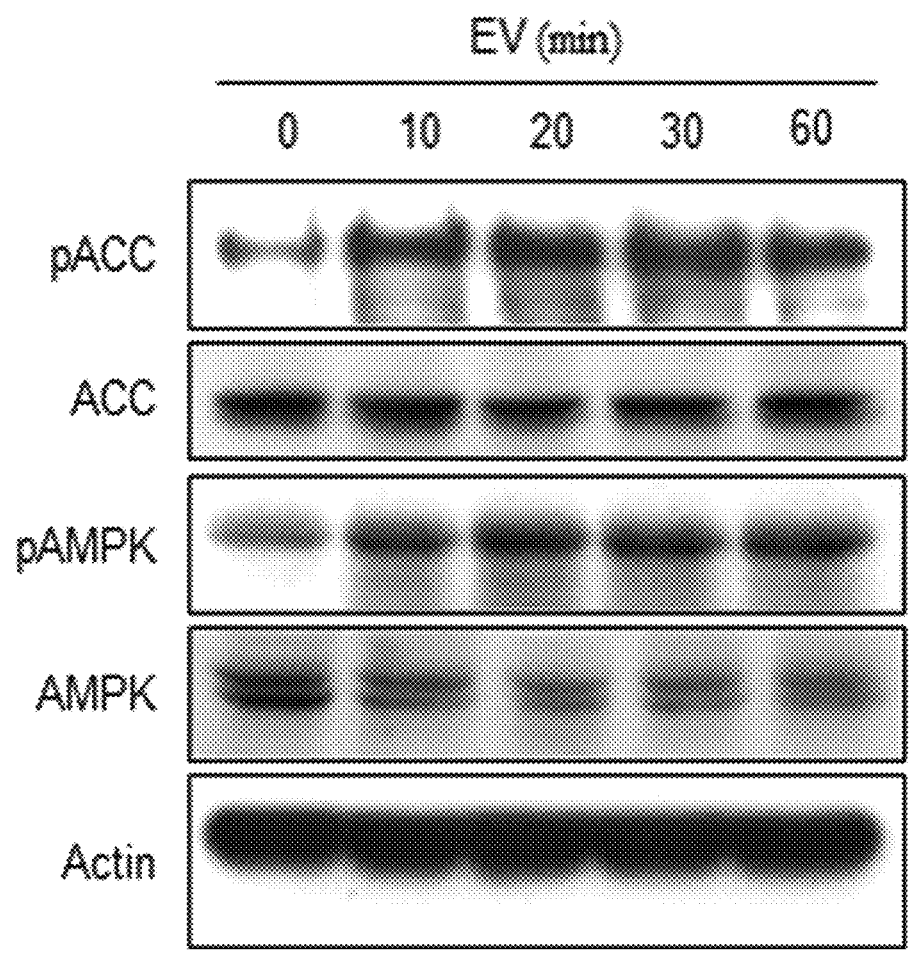
FIG. 16 illustrates a result obtained by confirming AMPK activation at varying times (10, 20, 30, and 60 minutes) after *Akkermansia muciniphila*-derived extracellular vesicles (EV) are administered to myocytes in vitro at a dose of 1 µg.

In addition, in order to evaluate AMPK activation over time for treatment with *Akkermansia muciniphila*-derived extracellular vesicles in vitro, myocytes were treated with extracellular vesicles at a concentration of 10 µg/ml for 0, 10, 20, 30, and 60 minutes. In a result obtained by measuring, by the western blot, the expression patterns of pAMPK and pACC, which are used as an important indicator in AMPK signal transduction, as shown in FIG. 16, it can be seen that an increase in the pAMPK and pACC expression starts at 10 minutes after treatment with extracellular vesicles and continues for 60 minutes.

Figure 17:
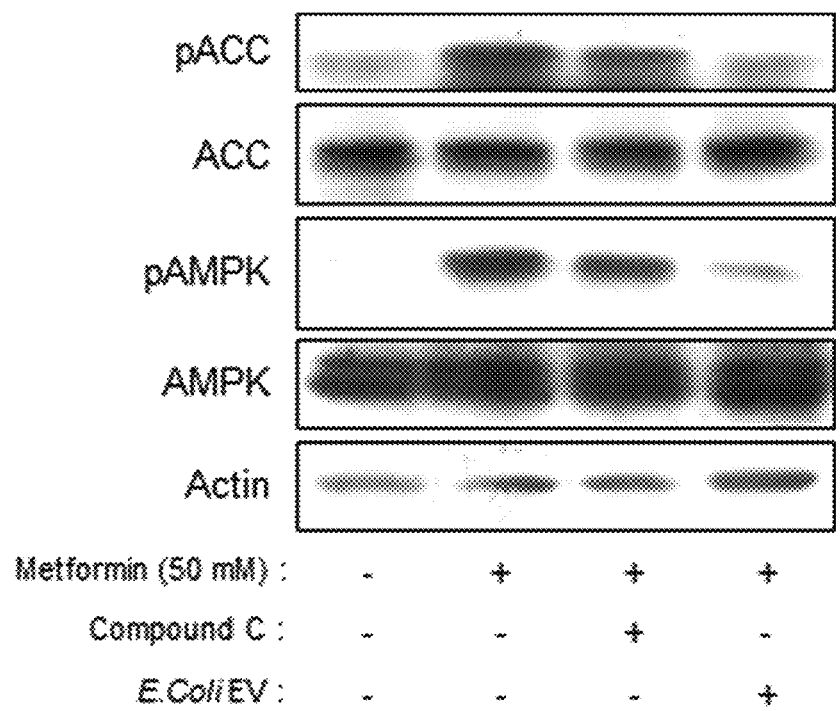
FIG. 17 illustrates a result obtained by confirming AMPK activation after metformin, an AMPK signal inhibitor (compound C), and *E. coli*-derived extracellular vesicles are respectively administered to myocytes in vitro.

Meanwhile, in order to further compare an influence of extracellular vesicles derived from bacteria other than the *Akkermansia muciniphila* on AMPK activation, myocytes were treated with *E. coli*-derived extracellular vesicles at a concentration of 10 μg/ml. In a result obtained by measuring, by the western blot, expression levels of pAMPK and pACC, which are used as an important indicator in AMPK signal transduction, as shown in FIG. 17, it can be seen that the expression levels of pAMPK and pACC remarkably decrease, demonstrating that the AMPK signal transduction is inhibited. On the other hand, the AMPK signal transduction was increased by metformin (therapeutic agent for diabetes) and decreased by compound C (AMPK signal transduction inhibitor).

EXAMPLE 8

Figure 18:
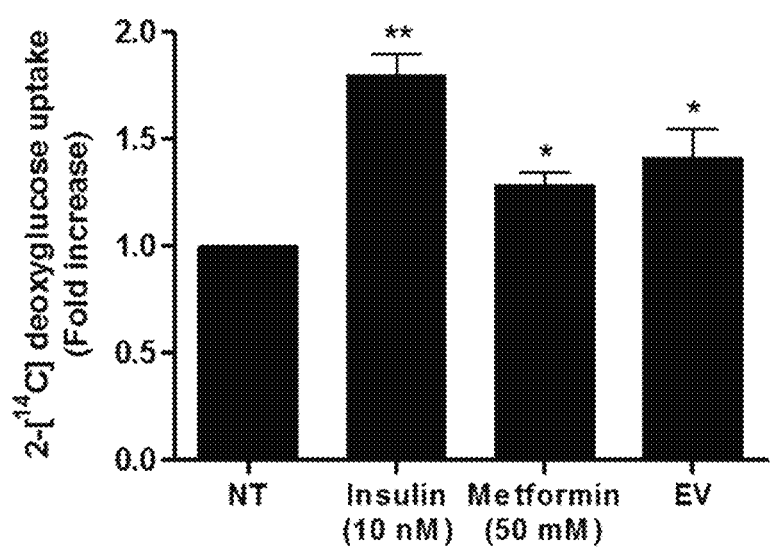
FIG. 18 illustrates a result obtained by comparing and evaluating the degree of glucose uptake after insulin, metformin, and *Akkermansia muciniphila*-derived extracellular vesicles (EV) are respectively administered to myocytes in vitro.

Influence of *Akkermansia muciniphila*-Derived Extracellular Vesicles on Glucose Uptake in Myocytes In order to evaluate an influence of *Akkermansia muciniphila*-derived extracellular vesicles on glucose uptake in myocytes, myocytes were treated with 10 μg/ml of *Akkermansia muciniphila*-derived extracellular vesicles in vitro for 1 hour, and glucose uptake was assessed using a radioisotope (2-[$^{14}$C]deoxyglucose). As a result, as shown in FIG. 18, it can be seen that, compared to a negative control (No Treatment (NT)), the glucose uptake in the myocytes was increased by *Akkermansia muciniphila*-derived extracellular vesicles (EV), which is similar in extent to a glucose uptake increase when a myocyte is treated with insulin (10 nm) or metformin (50 mM).

Figure 19:
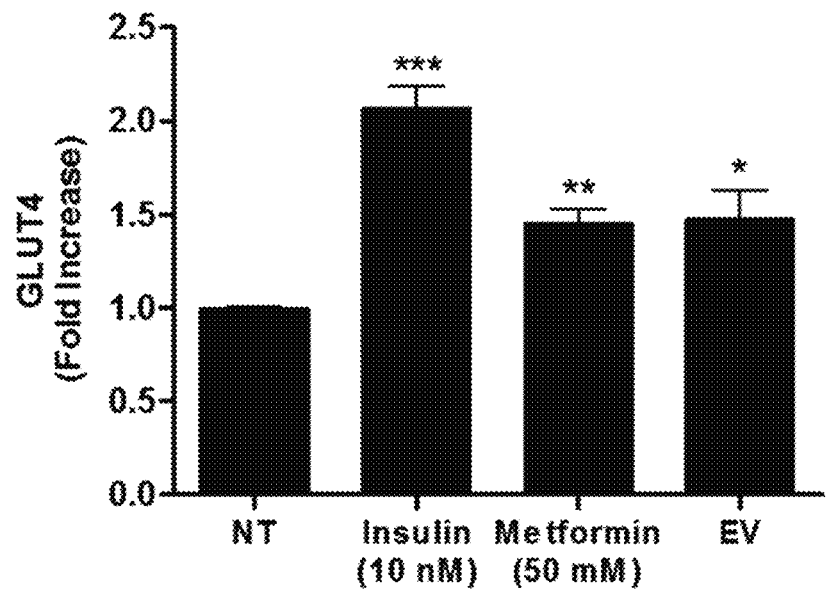
FIG. 19 illustrates a result obtained by comparing and evaluating the degree of expression of a GLUT4 transporter, a receptor for glucose uptake, after insulin, metformin, and *Akkermansia muciniphila*-derived extracellular vesicles (EV) are respectively administered to a myocyte in vitro.

In addition, in order to evaluate an influence *Akkermansia muciniphila*-derived extracellular vesicles on expression of a glucose transport protein (GLUT4 transporter) in myocytes, myocytes were treated with 10 μg/ml of *Akkermansia muciniphila*-derived extracellular vesicles in vitro for 1 hour, and then the degree of GLUT4 expression in a cell membrane was measured by an o-phenylenediamine (OPD) assay. As a result, as shown in FIG. 19, it can be seen that, compared to a negative control (No treatment (NT)), the GLUT4 expression was increased by *Akkermansia muciniphila*-derived extracellular vesicles (EV) which is similar in extent to the increased expression of GLUT4 when a myocyte is treated with insulin (10 nm) or metformin (50 mM).

Figure 20:
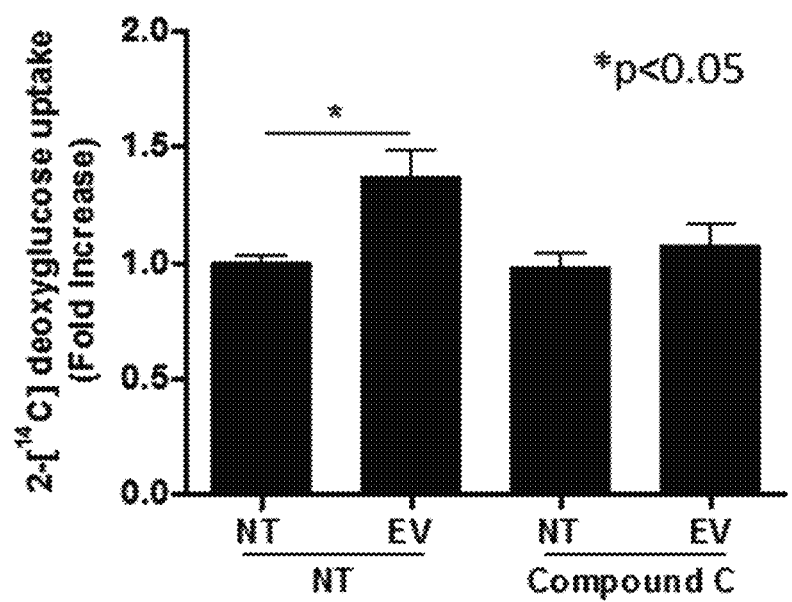
FIG. 20 illustrates a result obtained by confirming an effect of an AMPK signal inhibitor (compound C) on glucose uptake after *Akkermansia muciniphila*-derived extracellular vesicles (EV) are administered to myocytes in vitro.

In addition, in order to evaluate whether glucose uptake, which is increased by *Akkermansia muciniphila*-derived extracellular vesicles, is inhibited by AMPK signal transduction, myocytes were pretreated with compound C (AMPK signal transduction inhibitor), and then treated with 10 μg/ml of extracellular vesicles for 1 hour, followed by assessment of the glucose uptake using a radioisotope (2-[$^{14}$C]deoxyglucose). As a result, as shown in FIG. 20, it can be seen that the glucose uptake, which is increased by the *Akkermansia muciniphila*-derived extracellular vesicles, is decreased by compound C. This means that improvement of insulin resistance in myocytes by the *Akkermansia muciniphila*-derived extracellular vesicles is closely related to an AMPK signal transduction process.

While the present invention has been described above with reference to the exemplary embodiments of the present invention, it should be understood by those skilled in the art that various modifications and alterations may be made without departing from the spirit and scope of the present invention described in the appended claims.

The invention claimed is:

1. A method of alleviating obesity or diabetes comprising administering a food composition including *Akkermansia muciniphila*-derived extracellular vesicles as an active ingredient to a subject in need thereof, wherein the food composition is a fermented food composition prepared through fermentation by adding *Akkermansia muciniphila*.

* * * * *